(12) United States Patent
Benesh

(10) Patent No.: US 6,565,519 B2
(45) Date of Patent: May 20, 2003

(54) MACHINE AND METHOD FOR MEASURING SKELETAL MISALIGNMENTS IN THE HUMAN BODY

(75) Inventor: Peter Benesh, Monroe, MI (US)

(73) Assignee: Benesh Corporation, Monroe, MI (US)

( * ) Notice: Subject to any disclaimer, the term of this patent is extended or adjusted under 35 U.S.C. 154(b) by 125 days.

(21) Appl. No.: 09/813,757

(22) Filed: Mar. 21, 2001

(65) Prior Publication Data

US 2002/0138022 A1 Sep. 26, 2002

(51) Int. Cl.[7] ................................................. A61D 5/00
(52) U.S. Cl. ....................................................... 600/587
(58) Field of Search ............................ 128/781; 33/503, 33/174; 600/595, 581, 582; 364/567; 606/31

(56) References Cited

U.S. PATENT DOCUMENTS 5,088,504 A * 2/1992 Benesh et al. ............... 128/781
5,408,754 A * 4/1995 Raab ............................ 33/503

* cited by examiner

Primary Examiner—Henry Bennett
Assistant Examiner—Sabrina Dagostino
(74) Attorney, Agent, or Firm—Harness, Dickey & Pierce, P.L.C.

(57) ABSTRACT

An improved machine and method for measuring skeletal misalignments in the human body provides an indicator for simultaneously collecting and storing digital data corresponding to the deviation of the uppermost portion of each ilium from the frontal and transverse planes. The indicator may also collect and store digital data reflecting the position of various vertebrae.

16 Claims, 6 Drawing Sheets

US 6,565,519 B2

MACHINE AND METHOD FOR MEASURING SKELETAL MISALIGNMENTS IN THE HUMAN BODY

BACKGROUND OF THE INVENTION

The orthodox premise of chiropractic practice is defined as the correction, restoration toward normal, or replacement of misalignments of subluxated vertebrae by the act of adjusting such subluxated vertebrae to their normal, relative position. A subluxation is a condition caused by vertebrae misalignments. A subluxation results from the abnormal movement of sublaxated vertebra, which through pressure, or interference of an irritation producing mechanism detrimentally affects the nervous system. In particular, this pressure affects the spinal cord, which is lodged in the vertebral canal, and can cause abnormal functioning of the central nervous system. This may manifest itself in a variety of conditions and/or diseases in humans.

The present invention is based on the premise that the atlas vertebra, also known as "C-1", is the most important vertebra in the spinal column. This is because C-1 is the uppermost vertebra of the human spine, and thereby supports the skull in close proximity to the caudal region of the brain stem.

Observations in a large number of cases have shown that pelvic distortion is accompanied by, and correlates with some misalignment in the C-1 vertebrae, in one or more planes of its positional relationship to the occiput. It is desirable to be able to quickly, accurately, and reproducibly, measure these misalignments.

It has long been known to chiropractors that it is important to correct occiputal-atlanto-axial subluxations. Typically, in the past, correction of such subluxations has been accomplished by using X-rays as the primary source of information as to the location of C-1, and subjacent vertebrae and as to the positional relationship of C-1 to the occiput. In the prior normal routine, a series of X-rays were taken in the three planes of motion in which spinal vertebrae can abnormally move and a listing was prepared from an analysis of the degrees of abnormal motion. After adjustment, a second series of X-rays was taken and an appraisal made of the degree of correction of the misalignments.

Improvements in the apparatus to measure postural distortion-stress effects (upper thoracic and pelvic distortions) by means other than X-ray as described in U.S. Pat. Nos. 4,036,213, 4,033,329 and 5,088,504, provide information as to the effects of an atlas adjustment or the need for further adjustment. As a result, the need for X-rays to check skeletal misalignments is reduced. Thus, it would be desirable to provide further improvements in apparatus and technique for correlating postural distortion-stress effects with X-ray determination of misalignments to minimize the use of X-rays.

SUMMARY OF THE INVENTION

The present invention pertains to an improved machine and method for measuring skeletal misalignments in the human body. The invention provides an indicator for simultaneously collecting and storing digital data corresponding to the deviation of the uppermost portion of each ilium from the frontal and transverse planes. The indicator may also collect and store digital data reflecting the position of various vertebrae.

BRIEF DESCRIPTION OF THE DRAWINGS

The present invention will become more fully understood from the detailed description and the accompanying drawings, wherein.

DESCRIPTION OF THE PREFERRED EMBODIMENT

Figure 1:
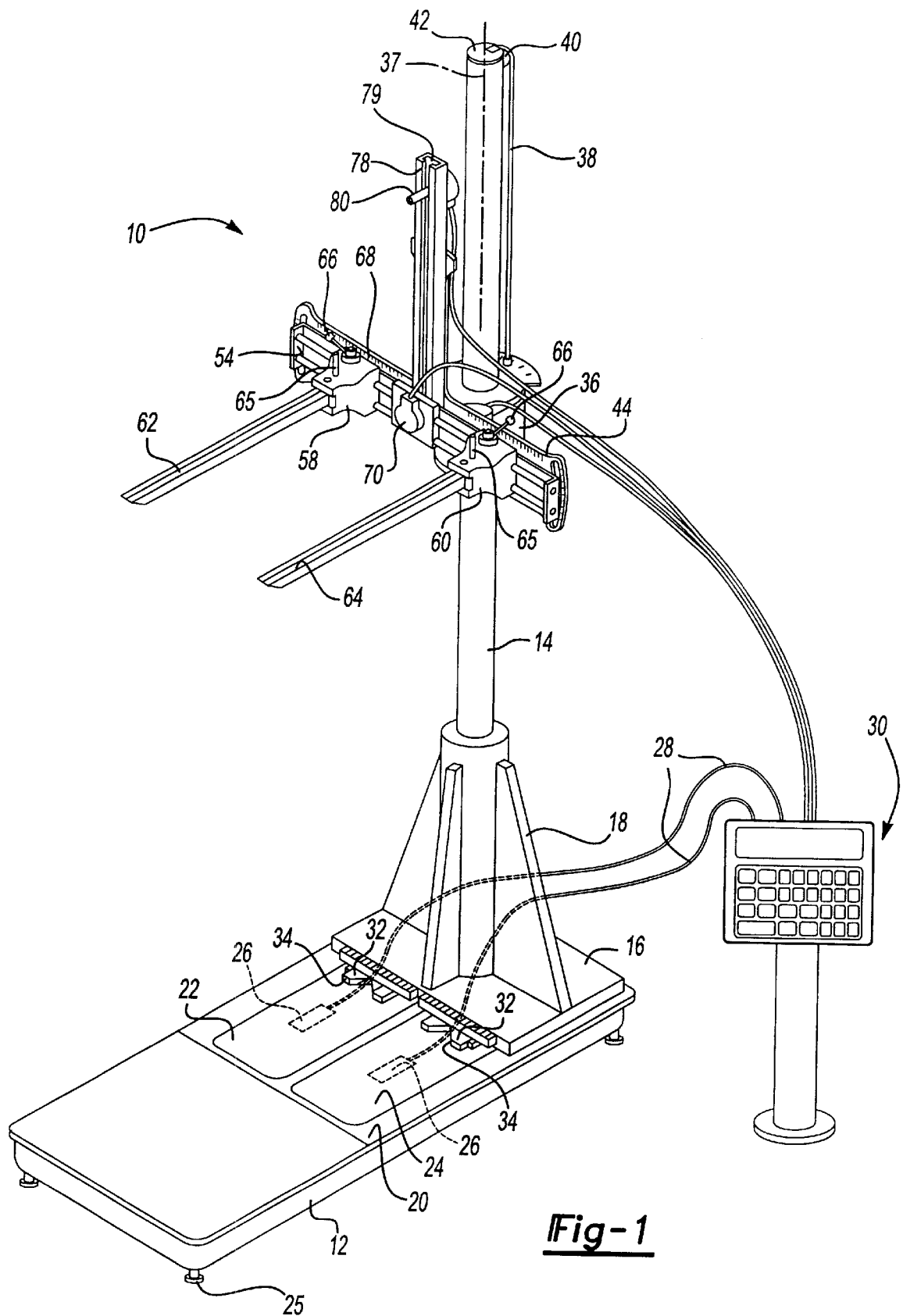
FIG. 1 is a perspective view of a skeleton checking machine embodying features of the present invention.

With reference to FIG. 1, a skeleton measuring machine constructed in accordance with the teachings of the present invention is generally depicted at reference numeral 10. Machine 10 includes a base 12 from which a vertically extending column 14 is supported and reinforced by a plate 16 and webs 18. Base 12 includes a top surface 20 extending substantially parallel to the ground. A first platform 22 and a second platform 24 are positioned within the base 12 for receiving the feet of a patient and for measuring the weight load placed on each of the patients feet. The platforms are positioned parallel to the ground by four adjustable leveling pads 25 located at the corners of base 12.

Pressure sensors 26 are located beneath each of the platforms 22 and 24 for converting the weight measurement sensed by each of the platforms into electrical impulses that are sent over lines 28 to an indicator 30. Indicator 30 reads each of the impulses and displays a digital weight readout. After skeletal adjustments are made, new readings may be taken on machine 10 to see if weight imbalance or other skeletal postural-distortions have been corrected. Locators 32 are mounted on platforms 22 and 24 for lateral movement thereon toward and away from each other in the horizontal plane. Locators 32 include heel-positioning flanges 34 for locating the body of a patient relative to the machine.

A hollow cylindrical sleeve 36 is slidably coupled to column 14 and is rotatable about a centerline 37 longitudinally extending through the center of column 14. Sleeve 36 is counterbalanced by a cable 38 which extends over a counterbalancing wheel 40 and secured to a weight (not shown) within the column. Wheel 40 is mounted on an angularly moveable cap 42 located in the top of column 14. A fixed plate 44 is secured to sleeve 36 and is movable vertically and angularly therewith.

Figure 2:
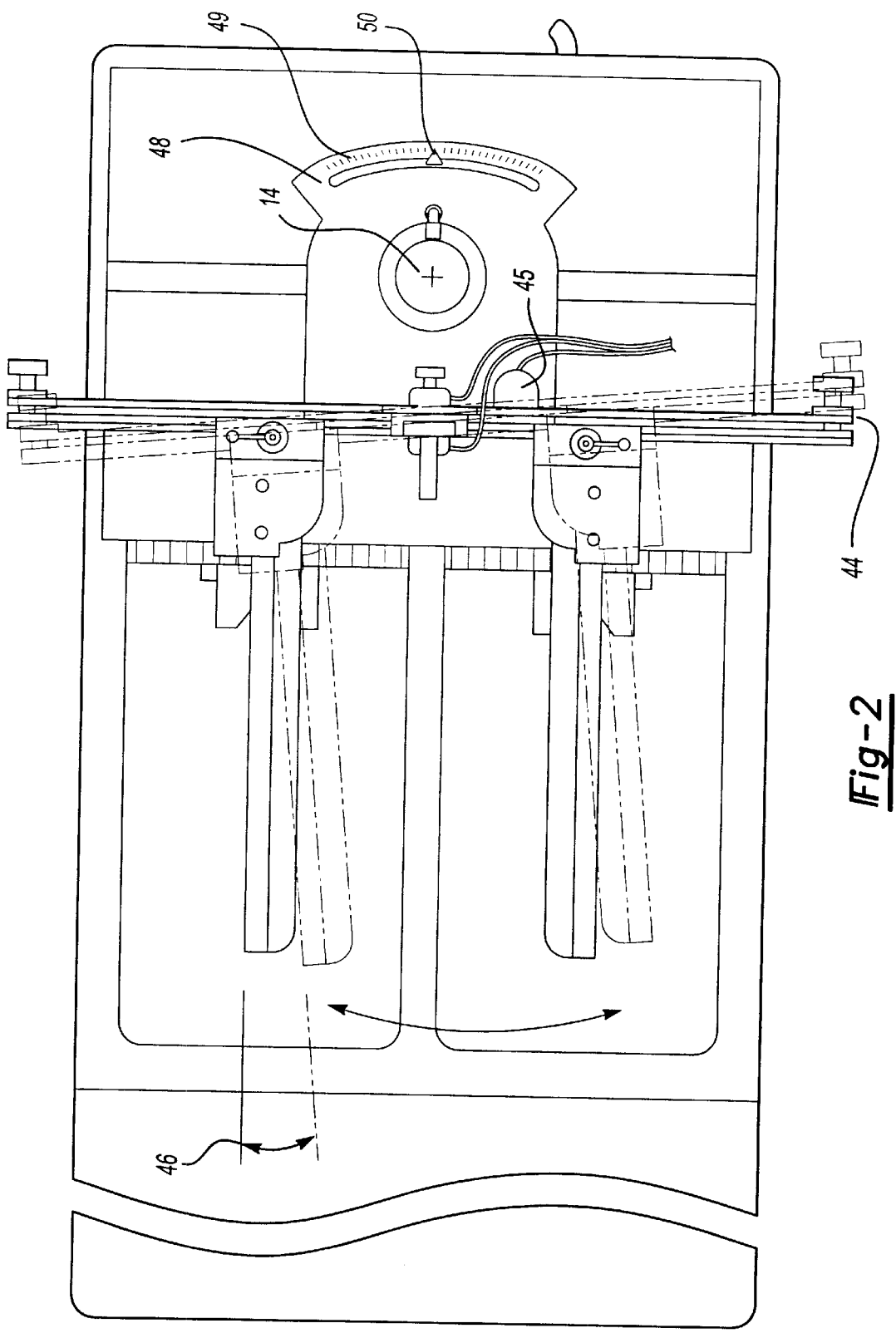
FIG. 2 is a plan view of the machine illustrated in FIG. 1.

With reference to FIG. 2, a first transducer 45 is mechanically coupled to cylindrical sleeve 36 having a reference relative to column 14. First transducer 45 is electrically coupled in communication with indicator 30. Preferably, first transducer 45 is an optical encoder capable of quantifying the angular movement of sleeve 36 relative to column 14 depicted as transverse angle 46. The optical encoder includes a small plastic disc having finely graduated lines positioned along its perimeter. A sensor counts the lines as the disc is rotated and digital data is output. Indicator 30 converts the digital data into useable information. The information is displayed on a screen 47 (FIG. 6) and may be selectively stored or printed.

A transverse indicating plate 48 includes a scale 49 by which the amount of angular movement may also be indicated. A finger 50 is secured to rotatable sleeve 36. Indicating plate 48 is keyed to column 14 which prevents plate 48 from rotating during operation. In this manner, transverse deviation may be measured in an analog manner using indicating plate 48 in conjunction with finger 50. It should be appreciated that it is an object of the present invention to be able to digitally retrofit machines originally equipped with only a pointer and an indicating plate.

Figure 3:
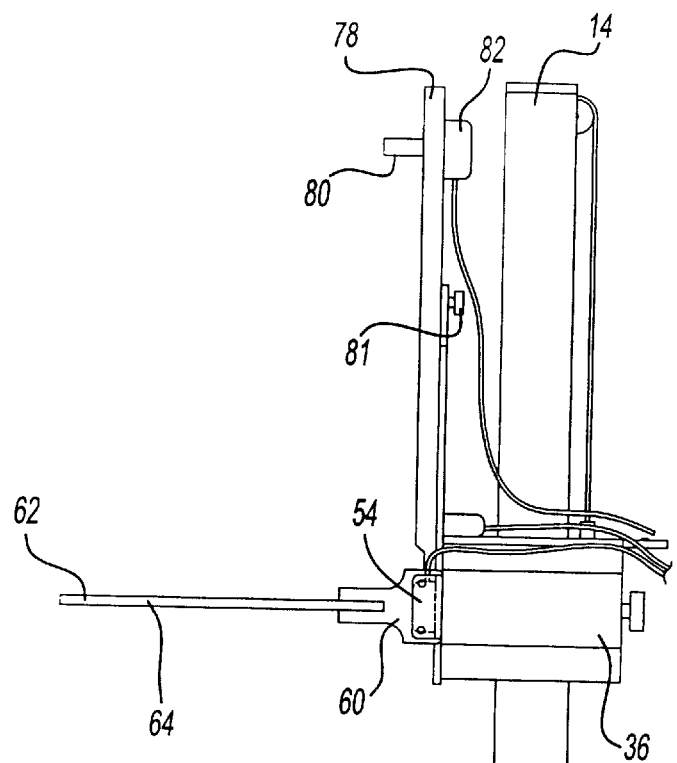
FIG. 3 is a side-elevational view of a skeleton checking machine constructed in accordance with the teachings of the present invention.
Figure 3:
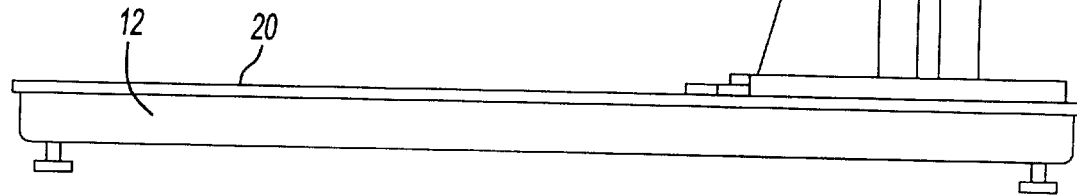
Figure 4:
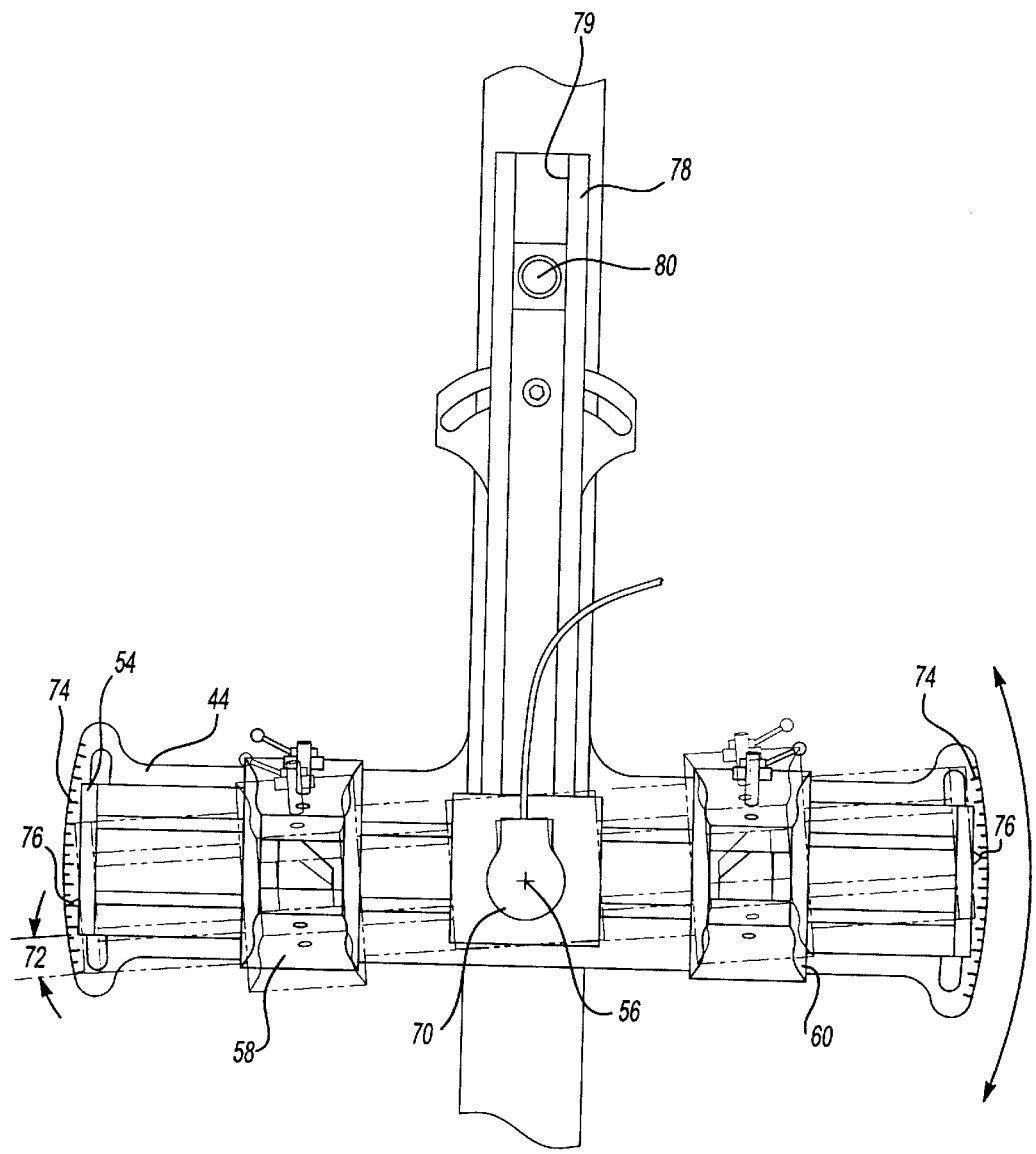
FIG. 4 is a front view of an indicator constructed in accordance with the teachings of the present invention.

As shown in FIGS. 3 and 4, a cross bar 54 is secured to fixed plate 44 by a pivot 56 positioned midway between the ends of cross bar 54. Right and left handed housings 58 and 60 are mounted on cross bar 54 for movement toward and away from each other. Specifically, housings 58 and 60 are kept in simultaneous counter-reciprocating relationship to each other by means of a rack and pinion (not shown). Because cross bar 54 is mounted to sleeve 36, housings 58 and 60 are also rotatably moveable in the horizontal plane. A pair of pelvic arms 62 and 64 are pivotally mounted to housings 58 and 60 in a horizontal plane. Accordingly, pelvic arms 62 and 64 may be locked in a parallel relation, as illustrated in FIGS., by means of a lever 65. Alternatively, lever 65 can lock pelvic arms 62 and 64 in a 45 degree position. By releasing levers 65, free range of lateral motion of pelvic arms 62 and 64 is attained.

Housings 58 and 60, and pelvic arms 62 and 64 are laterally locked in place by pelvic arm lock levers 66. Pelvic arm lock levers 66 are actuated by raising the levers 66, engaging a cam (not shown) which locks against both sides of rods (not shown) contained within cross bar 54. Pelvic arm lock levers 66 are located on top of right and left housings 58 and 60, as shown in the FIGS. Alternatively, lock levers 66 may be placed at the bottom of housings 58 and 60.

Arms 62 and 64 are movable toward and away from each other and upwardly and downwardly with sleeve 36 to reach a position where they rest upon the ilii of a patient. Once the arms 62 and 64 are so positioned, a reading on a scale 68 located on the top of cross bar 54 is taken. From the scale reading, locators 32 on each of the platforms 22 and 24 are adjusted toward or away from each other to insure that the weight of the body is carried on points immediately below the uppermost point of each ilium. Specifically, the position of locators 32 requires the feet of the patient to be separated a distance which conforms to the spacing of the ilii.

A second transducer 70 is coupled to cross bar 54 for determining a frontal inclination angle 72. Preferably, second transducer 70 is an optical inclinometer constructed to quantify small changes in angular position relative to the ground. Second transducer 70 is electrically coupled in communication with indicator 30. As will be described in greater detail hereinafter, an operator may direct indicator 30 to display, collect, print or store data provided by some or all of the transducers.

A frontal inclination angle reading may also be taken using a redundant analog pelvic scale 74. Pelvic scale 74 is located on both sides of fixed plate 44. Fingers 76 are located at both ends of cross bar 54 to indicate offset of the illii.

Figure 5:
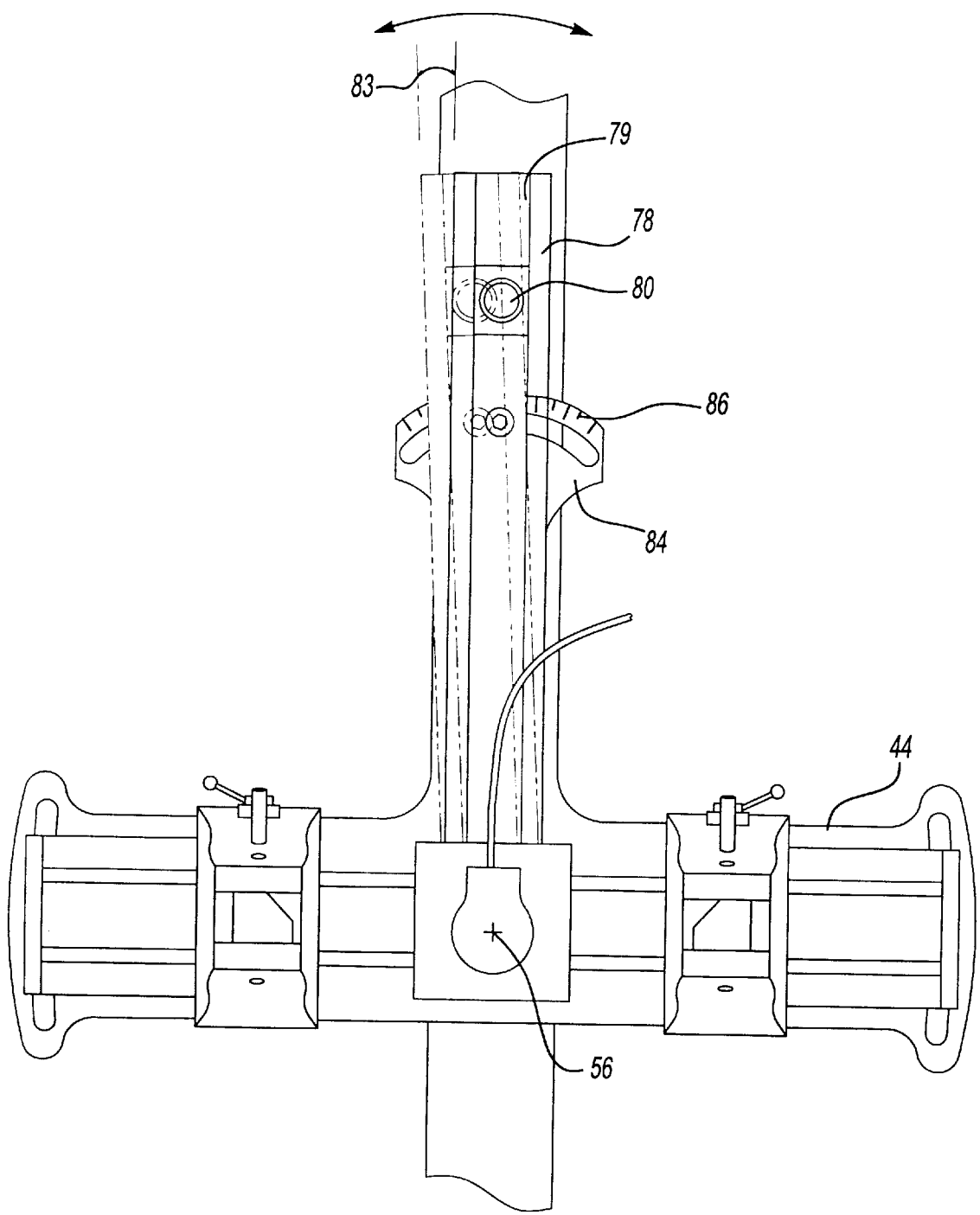
FIG. 5 is another front view of an indicator constructed in accordance with the teachings of the present invention.

As best shown in FIGS. 1, 3 and 5, a vertebral probe slide bar 78 defining a channel 79 is rotatably coupled to fixed plate 44. Vertebral probe slide bar 78 may be rotated about the centerline of pivot 56 and is locked in position by a vertebral probe lock 81. A laser 80 is slidingly disposed within channel 79 and coupled to vertebral probe slide bar 78. A third transducer 82 (FIG. 3) is coupled to vertebral probe slide bar 78 to determine a vertebral deviation angle 83. Third transducer 82 is preferably an optical inclinometer to measure changes in the angle of orientation of slide bar 78 in relation to the ground. Third transducer 82 is also electrically coupled in communication with indicator 30. Accordingly, data from third transducer 82 is available for collection once a command from indicator 30 is received.

Fixed plate 44 includes an upwardly extending portion 84 positioned adjacent to and behind vertebral probe slide bar 78. A scale 86 is imprinted upon upwardly extending portion 84 to provide an analog method of determining angular displacement of vertebral probe slide bar 78 relative to fixed plate 44.

The process of the invention involves determining the distortions in the lumbosacral area by determining deviations which may exist from the axes of the frontal and sagittal planes of the pelvic girdle. Specifically, a measurement is made of such deviations by positioning a human in a standing position on separate support surfaces for each foot and while the human is standing in an erect position, as nearly vertical as possible, the distance between the uppermost portion of each ilium is measured. For the purpose of determining an accurate deviation of the uppermost portion of each ilium from the axes of the frontal and sagittal planes, and for obtaining an accurate determination of weight distribution, it is important to insure that the spacing of the feet is such that the weight of the body is carried on points immediately below the uppermost point of each ilium. To insure such a condition, the center portion of each heel bone is positioned at a spacing such that the distance between the heel bones is identical to the distance between the uppermost portion of each ilium. Measurements are then made to determine whether the uppermost portion of each ilium lies in a single horizontal plane, or deviates there-from. Measurements of the distribution of weight are also taken. A determination is also made as to whether the uppermost part of each ilium lies in a frontal plane which is at right angles to the sagittal plane and any deviation therefrom is recorded. Such deviation actually constitutes a rotation of the plane of the upper part of each ilium.

Figure 6:
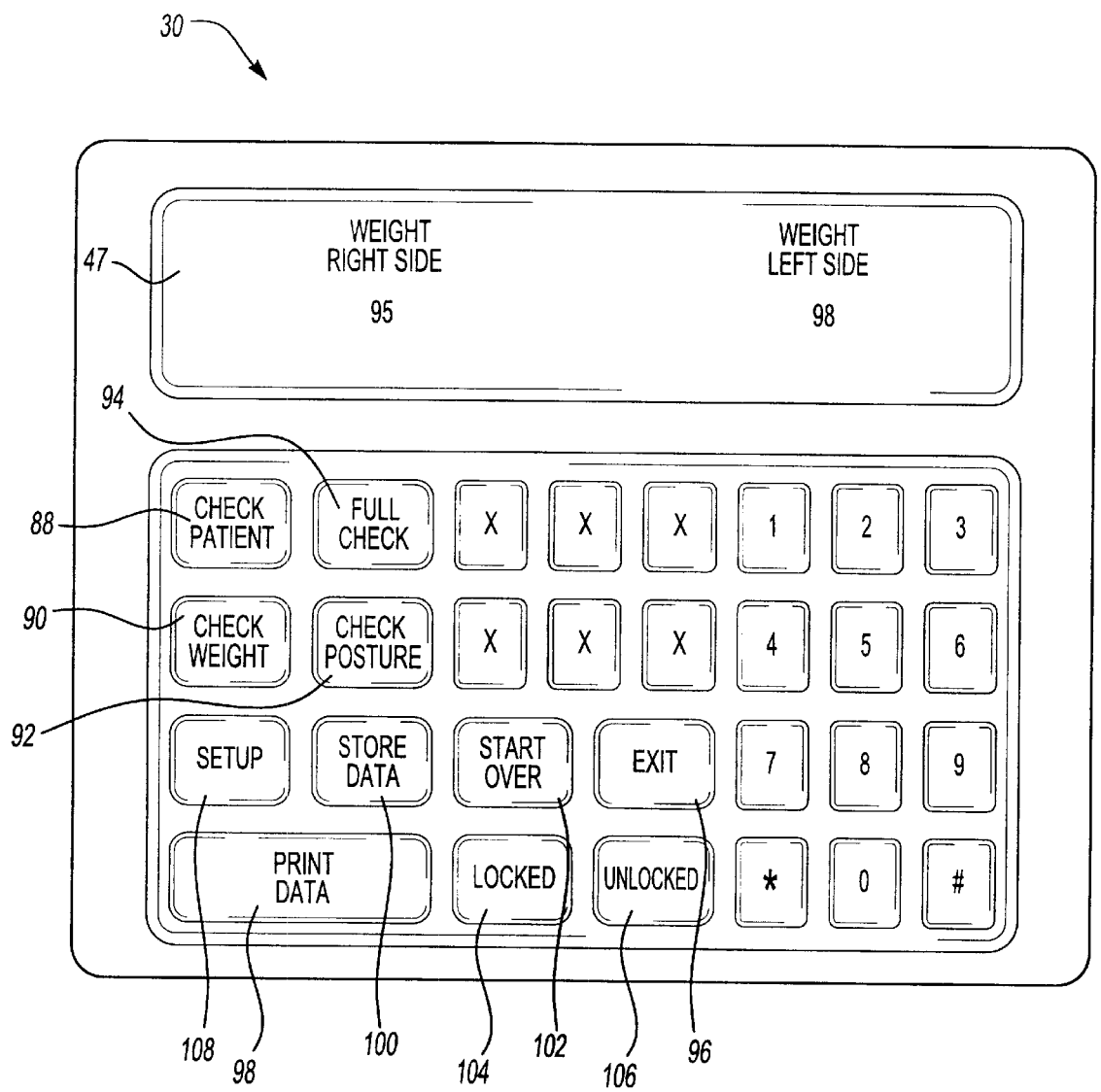
FIG. 6 is a partial plan view of an indicator screen constructed in accordance with the teachings of the present invention.

With reference to FIG. 6, the data collection system of the present invention allows an operator of machine 10 to simultaneously collect and record left leg weight, right leg weight, total weight, weight differential, percentage weight differential, transverse angle, frontal inclination angle and vertebral deviation angle. In this manner, errors previously introduced by a patient moving or shifting weight are avoided. Additionally, errors due to misreading scales or transcription are alleviated. At start-up, display screen 47 provides real time right and left weight data or the three posture data readings. The screen may be toggled back and forth by simply pressing a button located on indicator 30.

Indicator 30 operates primarily as a menu driven data collection system. It should be appreciated that indicator 30 provides a series of different screen displays depending upon the current location within the program. Accordingly, the use of the term "button", hereinafter does not necessarily correspond to a physical device but may simply be a portion of screen 47 or indicator 30. For example, if the "CHECK PATIENT" button 88 is pressed, a submenu of options including "CHECK WEIGHT" 90, "CHECK POSTURE" 92, "FULL CHECK" 94, or "EXIT" 96. If "CHECK WEIGHT" 90 is chosen, the display will request that the patient number be input. After entering the patient number, the display will prompt the user to define a "pre" or "post" treatment check. After the choice has been made, the indicator will take an average of both scales. The data can then be reviewed. The indicator will display all right and left weight data points collected and then seek further instructions. The operator may then choose "PRINT DATA" 98, "STORE DATA" 100, "START OVER" 102, or "EXIT" 96.

If the "CHECK POSTURE" option is chosen, the indicator will dynamically display the three posture readings. The frontal, transverse, and vertebral deviation readings may be locked or unlocked by pressing buttons 104 and 106. A locked reading will not dynamically update unless subsequently unlocked. After the readings have been locked in, the display will show the same options of print data, store data, re-do posture, and exit.

"FULL CHECK" button 94 directs indicator 30 to collect both weight readings and all three posture angles in a substantially simultaneously manner.

"PRINT DATA" button 98 allows an operator to display current visit data, previous visit data, all visits or exit. Additionally, data from more than one patient may be accessed and printed.

Finally, the pressure sensors and optical encoders may be calibrated by pressing "SET UP" 108. A series of menu prompts may be selected to zero out the scales, encoders, or both. The correct weight for both scales may also be input to recalibrate the scales.

When the above measurements have been made, and an adjustment is made to the appropriate vertebrae, a post measurement is taken to determine whether a distortion of the pelvis still exists. This determination is made by positioning each foot on the supports, determining the location of the uppermost part of each ilium relative to the vertical axis, i.e., the axes of the frontal and sagiftal planes, and making a comparison between the locations so determined and the locations determined prior to the adjustment of the appropriate vertebrae.

The process of this invention is useful for checking the degree of correction of spastic contracture resulting from an atlas adjustment shortly after the adjustment is made, in a similar manner, it is particularly useful in checking for pelvic distortion with the passage of time after an adjustment, without repeat X-rays.

The machine 10 and process of the present invention is unique in determining the absence or the degree of the presence of interference with nervous conduction at the spinal level of the top cervical vertebrae (C-1) as expressed in terms of weight distribution and bodily distortions. It determines whether an adjustment thereof is required. It measures the effectiveness of such adjustment immediately following such adjustment and the degree to which it is corrective and, on succeeding checks, the length of time the correction remains stabilized. The machine also measures the state and degree of muscular and/or skeletal stress of the body. It measures the degree of pelvic-girdle distortion into the frontal, sagittal and transverse planes (orientation) of motion so that relationships to the misalignments of vertebrae into the frontal, sagittal and transverse planes can be established and compared. The machine indicates the influence of fatigue, stress, and other debilitating factors on the body in terms of bodily distortions. It predicts the onset of a vertebral subluxation and indicates changes in the misalignments of a vertebral subluxation indicative of the need for correction vector changes in the adjustment and a reevaluation of the subluxation listing.

The machine 10 reduces the need for unnecessary X-ray exposure by providing a means by which to determine if a trauma suffered by the patient since the original X-rays were taken was sufficient to change the original subluxation listing. The machine can measure changes in the weight distribution and in the height of the crests of the pelvis before and after a vertebral adjustment, and record deviations of individual vertebral segments in relation to the pelvic-girdle, as well as the effects of a vertebral adjustment on such deviations. The machine provides a measurable means of establishing the patients' progress in terms of weight distribution, bodily distortion, positive evidence of improvements, no improvement, or regression. The machine provides a data retrieval system based on measurement for comparing the patient's symptoms with body stress and can indicate whether a subluxation has been reduced to 0 degrees in all planes.

It will be appreciated that the recorded deviations of weight distribution and of the pelvic girdle region, as above described, can be readily repeated at any time it is desired to recheck the relative location of the vertebrae which may have been previously determined and recorded by merely following the above described steps in the same order and under the same conditions as expressed. The present invention thus provides an easy, fast, inexpensive but reliable machine and procedure for accurately determining the patient's relative weight distribution, and also for determining the location of key vertebrae in humans. These measurements may be repeated without the necessity for additional X-ray photographs of the various planes of possible motion of the atlas vertebrae.

It should be recognized that while the above description constitutes the preferred embodiments of the present invention, the invention is susceptible to modification, variation, and change without departing from the proper scope and fair meaning of the accompanying claims.

What is claimed is:

1. A machine for checking skeletal and postural distortion comprising:
    an indicator;
    a pair of platforms to receive the feet of a patient, each of said platforms coupled to a sensor to determine the amount of said patients' weight resting on each platform;
    a pair of arms extending horizontally above said platforms, each arm selectively engaging the top of each ilium of said patient;
    a frontal plane transducer coupled to said pair of arms to determine a frontal plane deviation angle, said frontal plane transducer in communication with said indicator;
    a transverse plane transducer coupled to said pair of arms to determine a transverse plane deviation angle, said transverse plane transducer in communication with said indicator, whereby said indicator selectively collects and displays data received from said frontal plane transducer and said transverse plane transducer.

2. The machine of claim 1 further including a vertebral deviation transducer and a neck probe, said neck probe being selectively moveable above said pair of arms, said vertebral deviation transducer coupled to said neck probe and in communication with said indicator, whereby said indicator selectively collects and stores data from said vertebral deviation transducer.

3. The machine of claim 2 wherein said indicator simultaneously collects data from said sensors, said frontal plane transducer, said transversal plane transducer and said vertebral deviation transducer.

4. The machine of claim 3 wherein said indicator is operable to selectively collect and store data from more than one patient.

5. The machine of claim 4 wherein said frontal plane transducer is an optical encoder.

6. The machine of claim 5 wherein said frontal plane transducer is an inclinometer.

7. The machine of claim 1 wherein said indicator includes a screen to display data received from said frontal plane transducer.

8. The machine of claim 1 wherein said indicator includes a menu driven user interface to display data collection and storage options.

9. A method for determining skeletal deviation in a human being, the method comprising the steps of:

positioning a human on a pair of platforms, one platform supporting each foot; and substantially simultaneously determining the weight of each foot placed on each platform while determining deviation of the uppermost portion of each ilium from the frontal and transverse planes.

10. The method of claim 9 wherein the step of determining deviation from the frontal plane includes retrieving data collected by a first transducer.

11. The method of claim 10 wherein the step of determining deviation from the transverse plane includes retrieving data collected by a second transducer.

12. The method of claim 11 further including the step of determining a vertebral deviation from the sagittal plane.

13. The method of claim 9 further including the step of electronically transferring data corresponding to said deviation from the frontal and transverse planes to an indicator.

14. The method of claim 13 further including the step of selecting an option supplied by a menu driven software system to instruct said indicator.

15. The method of claim 14 wherein said option includes storing said weight of each foot and said deviation from the frontal and transverse planes.

16. The method of claim 15 wherein said option includes displaying a history of data previously collected.

* * * * *

UNITED STATES PATENT AND TRADEMARK OFFICE
CERTIFICATE OF CORRECTION

PATENT NO. : 6,565,519 B2
DATED : May 20, 2003
INVENTOR(S) : Peter Benesh

It is certified that error appears in the above-identified patent and that said Letters Patent is hereby corrected as shown below:

<u>Title page,</u>
Item [56], References Cited, add the following references:
-- U.S. PATENT DOCUMENTS:
| | | |
|---|---|---|
| 2,021,566 | 11/1935 | Millard |
| 2,111,648 | 3/1938 | Stone |
| 2,324,672 | 7/1943 | Bierman et al. |
| 2,810,964 | 10/1957 | Engelbert |
| 2,930,133 | 3/1960 | Thompson |
| 3,027,761 | 4/1962 | Lauro |
| 3,336,917 | 8/1967 | Pile et al. |
| 3,575,159 | 4/1971 | Pile et al. |
| 3,955,285 | 5/1976 | Moeckl |
| 4,033,329 | 7/1977 | Gregory et al. |
| 4,036,213 | 7/1977 | Gregory |
| 4,221,213 | 9/1980 | Gregory et al. |
| 4,914,611 | 4/1990 | Yamanaka et al. |

FOREIGN PATENT DOCUMENTS:
| | | |
|---|---|---|
| 0245098 | 11/1987 | EPO |
| 0028619 | 2/1987 | Japan |
| 8001419 | 10/1981 | Netherlands |

<u>Column 2,</u>
Line 27, "patients" should be -- patient's --;

<u>Column 3,</u>
Line 20, "FIGS." should be -- FIGS. 1 and 2 --;
Line 57, "illii" should be -- ilii --;

UNITED STATES PATENT AND TRADEMARK OFFICE
CERTIFICATE OF CORRECTION

PATENT NO. : 6,565,519 B2
DATED : May 20, 2003
INVENTOR(S) : Peter Benesh

It is certified that error appears in the above-identified patent and that said Letters Patent is hereby corrected as shown below:

Column 5,
Line 11, "simultaneously" should be -- simultaneous --;
Line 28, "sagiftal" should be -- sagittal --.

Signed and Sealed this

Thirteenth Day of January, 2004

JON W. DUDAS
*Acting Director of the United States Patent and Trademark Office*